US009861302B1

(12) United States Patent
Chatterjee et al.

(10) Patent No.: US 9,861,302 B1
(45) Date of Patent: Jan. 9, 2018

(54) DETERMINING RESPIRATION RATE FROM A VIDEO OF A SUBJECT BREATHING

(71) Applicant: Xerox Corporation, Norwalk, CT (US)

(72) Inventors: Avishek Chatterjee, West Bengal (IN); Prathosh Aragulla Prasad, Karnataka (IN); Pragathi Praveena, Karnataka (IN)

(73) Assignee: Xerox Corporation, Norwalk, CT (US)

( * ) Notice: Subject to any disclaimer, the term of this patent is extended or adjusted under 35 U.S.C. 154(b) by 29 days.

(21) Appl. No.: 15/197,080

(22) Filed: Jun. 29, 2016

(51) Int. Cl.
*G06K 9/00* (2006.01)
*A61B 5/113* (2006.01)
*G06T 7/20* (2017.01)
*A61B 5/00* (2006.01)

(52) U.S. Cl.
CPC .......... *A61B 5/113* (2013.01); *A61B 5/0013* (2013.01); *A61B 5/0077* (2013.01); *A61B 5/7225* (2013.01); *A61B 5/7246* (2013.01); *G06T 7/20* (2013.01); *G06T 2207/10016* (2013.01); *G06T 2207/10024* (2013.01); *G06T 2207/30004* (2013.01); *G06T 2207/30196* (2013.01)

(58) Field of Classification Search
None
See application file for complete search history.

(56) References Cited

PUBLICATIONS

Beauchemin, S., et al., "The Computation of Optical Flow", ACM Computing Surveys, Sep. 1995, pp. 433-467, vol. 27, No. 3.
Lucas, B., et al., "An Iterative Image Registration Technique with an Application to Stereo Vision", Proceedings of Image Understanding Workshop, Aug. 24-28, 1981, pp. 121-130.
Baker, S., et al., "A Database and Evaluation Methodology for Optical Flow", International Journal of Computer Vision, Mar. 2011, pp. 1-31, vol. 92, No. 1.
Horn, B., et al., "Determining Optical Flow", Massachusetts Institute of Technology, Artificial Intelligence Laboratory, Apr. 1980, pp. 1-28.
Fleet, D., et al., "Optical Flow Estimation", Appears in "Mathematical Models in Computer Vision: The Handbook", N. Paragios. Y. Chen, and O. Faugeras (editors), Chapter 15, 2005, pp. 239-258.

(Continued)

*Primary Examiner* — Atiba O Fitzpatrick
(74) *Attorney, Agent, or Firm* — Philip E. Blair; Fleit Gibbons Gutman Bongini & Bianco P.L.

(57) ABSTRACT

What is disclosed is a system and method for determining a respiration rate from a video of a subject breathing. One embodiment of the present method involves the following. A video is received of a subject breathing which comprises a first portion of N image frames, and a second portion of M image frames, N+M=T and N≥10 seconds of video. For each image frame of the first portion, flow vectors $F_t$ are determined for each (x,y) pixel location. A correlated flow field V is then calculated for the first portion of video. For each image frame of the second portion, flow vectors $F_t(x,y)$ are determined for each (x,y) pixel location and a projection of $F_t$ along V is calculated to obtain a velocity of thoracoabdominal motion in the direction of V. The velocity is integrated to obtain an integrated signal. Respiration rate is determined from the integrated signal.

18 Claims, 6 Drawing Sheets

(56) References Cited

PUBLICATIONS

Aires, K, et al., "Optical Flow Using Color Information: Preliminary Results", Proceedings of the 2008 ACM Symposium on Applied Computing, Mar. 16-20, 2008, pp. 1-5.

Barron, J.L., et al., "Performance of Optical Flow Techniques", International Journal of Computer Vision, Feb. 1994, pp. 1-60, vol. 12, No. 1.

U.S. Appl. No. 14/969,147, filed Dec. 15, 2015.

DETERMINING RESPIRATION RATE FROM A VIDEO OF A SUBJECT BREATHING

TECHNICAL FIELD

The present invention is directed to systems and methods for determining a respiration rate from a video of a subject breathing.

BACKGROUND

Respiration rate refers to the number of breathing cycles per minute. It is one of the important vital signs and frequently measured during the diagnosis and treatment of many pulmonary dysfunctions. Typically, in healthy adults the respiration rate ranges from 5 to 35 breaths per minute. The deviation of respiration rate from this usual range is indicative of pulmonary diseases like asthma, chronic obstructive pulmonary disease, tuberculosis, respiratory-tract infection, etc. Further, abnormally high respiration rate is an indication of pneumonia in children or tissue hypoxia associated to sleep apnea. Such pulmonary diseases cause about 18% of human deaths in the world. Often irregularities in respiration rate are also indicative of cardiac malfunctioning. Respiration rate is routinely measured for clinical diagnosis in many primary health care centers. Besides, measurement of respiration rate in an intensive care unit (ICU) directly ascertains whether the patient is breathing or not. Moreover, measurement of respiration rate can also be used for the analysis of human emotions such as anger or stress.

There exist a number of techniques for respiration rate measurement, including spirometry, impedance pneumography and plethysmography. However, these methods employ the use of contact based probes in the forms of leads or straps. Such contact-based methods are often prohibitive in many situations. They not only cause discomfort or irritation, particularly to sensitive skins, often patients change their normal breathing pattern during the monitoring with such contact-based methods. It can also be difficult to use such methods in neonates ICU or home monitoring. Further, during gated radiography it is not possible to use contact based measurements as they directly interfere with the radiography. Due to these reasons, non-contact RR measurement is becoming an emerging and immensely important problem in bio-medical engineering community.

Accordingly, what is needed in this art are sophisticated systems and methods for determining a respiration rate from a video of a subject breathing.

BRIEF SUMMARY

What is disclosed is a system and method for determining a respiration rate from a video of a subject breathing. One embodiment of the present method involves receiving a video of a subject breathing. The received video comprises at least T time-sequential image frames captured of an area of the subject where a signal corresponding to respiratory function can be registered by at least one imaging channel of an imaging device used to capture that video. The video has a first portion comprising at least 10 seconds of video and a second portion comprising M image frames. A flow vector $F_t$ is then determined for each (x, y) pixel location in each image frame $I_t$ of the first portion of the video. Once the flow vectors have been determined for each pixel location, a correlated flow field V is then determined for the entire first portion of the video. The correlated flow field captures how the individual flow vectors in each image frame are correlated to each other. For each image frame of the second portion of the video, a flow vector $F_t$ is determined for each respective (x,y) pixel location and a projection of $F_t$ is calculated in a direction of the correlated flow field V to obtain a velocity $vel_t$ on a per-frame basis. The velocities are then integrated over the duration of the second portion of the video to obtain an integrated signal corresponding to thoracoabdominal movement. A respiration rate is determined for the subject from the integrated signal over the timeframe of the second portion of the video, in seconds.

Features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for determining a respiration rate from a video of a subject breathing.

Non-Limiting Definitions

"Respiratory function" is a process of inspiration and expiration followed by a brief post-expiratory pause.

A "subject" refers to a living being. Although the term "person" or "patient" may be used throughout this disclosure, it should be appreciated that the subject may be something other than a human such as, for example, a primate. Therefore, the use of such terms is not to be viewed as limiting the scope of the appended claims strictly to humans.

A "video", as generally understood, is a plurality of time-sequential image frames. The video is captured of an area of the subject where a signal corresponding to respiratory function can be registered by at least one imaging channel of an imaging device used to capture that video. The video comprises a first portion and second portion. The first portion of the video is of at least 10 seconds in duration for a total of N image frames. The second portion of the video has M image frames, where N+M=T. The second portion of video can be any duration such as a few seconds, and may even comprise the frames of the first portion of the video.

Figure 1:
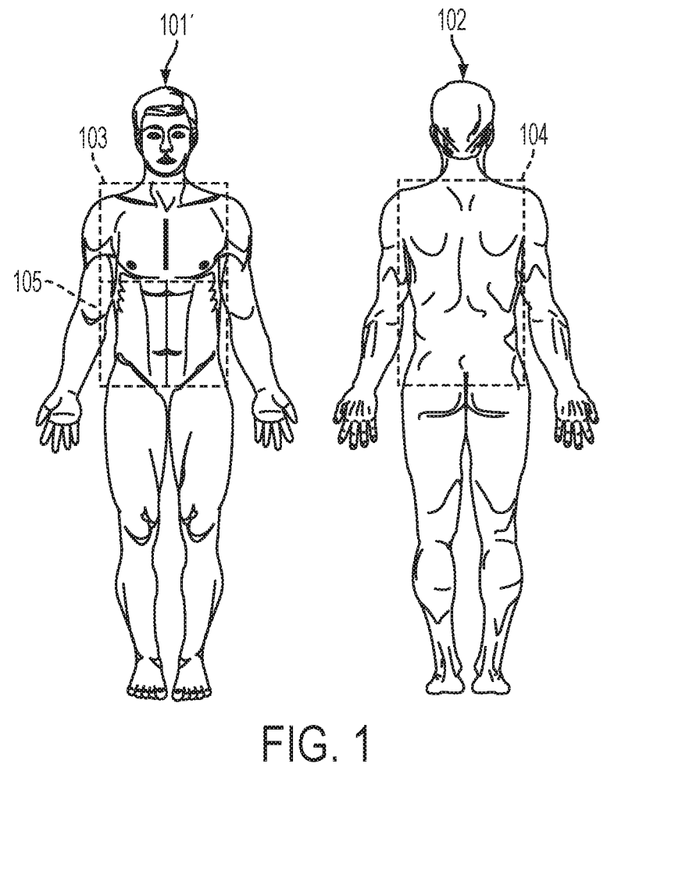
FIG. 1 shows an anterior view of an adult human as well as a posterior view wherein various areas of the subject where a signal corresponding to respiratory function can be obtained.

FIG. 1 shows an frontal view 101 of an adult human as well as a rear view 102. Example areas of the subject's body where a signal corresponding to respiratory function can be obtained from a video are shown at 103, 104, and 105. A signal corresponding to respiratory function can also be obtained from a lateral (side) view of the thoracic cage and abdomen. The appending claims should not be limited to obtaining a respiratory signal only from the body areas shown by way of example in FIG. 1. Moreover, the subject may be wearing clothing or covered by a sheet during video acquisition. Pixels in each of the image frames may be grouped, averaged, or pre-processed as desired to obtain more accurate measurements. Image frames may be pre-processed as needed to compensate for motion induced blurring, imaging blur, noise and other anomalies. Image frames may be deleted from a video as needed to decrease the frame rate. The video may also contain other components such as audio, time, date, reference signals, frame rate, and the like. The video may be processed to compensate for motion induced blur, imaging blur, slow illuminant variation or to enhance contrast or brightness. The video is captured by a video imaging device.

Figure 2:
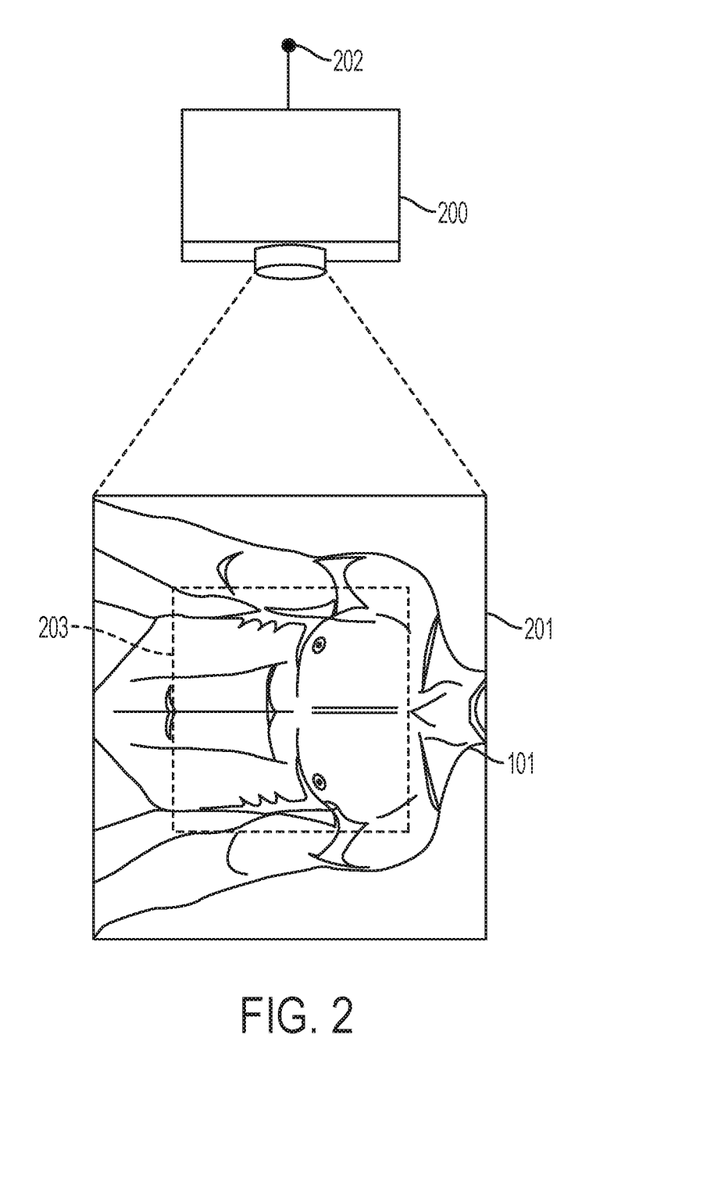
FIG. 2 shows an example video imaging device capturing time-sequential image frames of an area of the subject of FIG. 1.

A "video imaging device" or simply "imaging device", refers to a single-channel or multi-channel camera for capturing or otherwise acquiring temporally successive images. Imaging devices for acquiring video include a color video camera, a monochrome video camera, an infrared video camera, a multispectral video imaging device, a hyperspectral video camera, and a hybrid device comprising a combination hereof. FIG. 2 shows an example video imaging device 200 capturing time-sequential image frames (individually at 201) of an area 203 of the subject of FIG. 1. The video imaging device has a communication element 202 (shown as an antenna) which effectuates a communication with a remote device such as a workstation over a wireless network where the image frames are received for processing in accordance with the methods disclosed herein. The video imaging device has one or more lens which focus received reflected light on to photodetectors which record intensity values at pixel locations along a multi-dimensional grid. The received light is spatially resolved to form an image. Video imaging devices comprising standard video equipment and those with specialized imaging sensors are available from a wide array of vendors in various streams of commerce. The video imaging device may incorporate memory, a storage device, and a video analysis module comprising one or more microprocessors for executing machine readable program instructions for processing the received video in accordance with the teachings hereof. Such a video analysis module may comprise, in whole or in part, a software application working alone or in conjunction with one or more hardware resources. The captured video is received for processing.

"Receiving a video" is intended to be widely construed and includes retrieving, capturing, acquiring, or otherwise obtaining video image frames for processing. The video can be received or retrieved from a remote device over a network, or from a media such as a CDROM or DVD. The video can be received directly from a memory or storage device of the imaging device used to capture or acquire the video. Video may be downloaded from a web-based system or application which makes video available for processing. Video can also be received from an application such as those which are available for handheld cellular devices or handheld computing device such as an iPad or Tablet-PC. The received video is processed to obtain a signal which corresponds to thoracoabdominal movement.

Introduction to Optical Flow

The concept of optical flow was introduced by James J. Gibson in the 1940's to help understand and describe the role visual stimulus plays in the perception of movement in the mind of an observer. Gibson postulated that sequences of ordered images allow the estimation of motion as either instantaneous image velocities or discrete image displacements. A tutorial is disclosed in: "*Handbook of Mathematical Models in Computer Vision*", Paragios et al., Springer (2006), ISBN-13: 978-0387263717, [See, chapter: "*Optical Flow Estimation*", by David J. Fleet and Yair Weiss, which provides an introduction to gradient based optical flow analysis].

Optical flow analysis tries to calculate motion between two image frames which are taken at times t and t+Δt at various pixel locations common to both images or at locations of groups of pixels common to both images. These methods are often referred to as differential methods since they are based on local Taylor series approximations, i.e., they use partial derivatives with respect to the spatial and temporal coordinates. Generally, for a 2D+t dimensional case (3D or n-D cases are similar) values in the image at location (x, y) having intensity $I_t(x, y)$ will have moved an amount given by Δx, Δy and Δt between two image frames, such that:

$$I_t(x,y) = I(x+\Delta x, y+\Delta y, t+\Delta t) \tag{1}$$

Assuming the movement is small, the respective Taylor series can be given as:

$$I(x+\Delta x, y+\Delta y, t+\Delta t) = I(x, y, t) + \frac{\partial I}{\partial x}\Delta x + \frac{\partial I}{\partial y}\Delta y + \frac{\partial I}{\partial t}\Delta t + \ldots \tag{2}$$

From Eqs. (1) and (2), it follows that:

$$\frac{\partial I}{\partial x}\Delta x + \frac{\partial I}{\partial y}\Delta y + \frac{\partial I}{\partial t}\Delta t = 0 \tag{3}$$

which results in:

$$\frac{\partial I}{\partial x}V_x + \frac{\partial I}{\partial y}V_y + \frac{\partial I}{\partial t}V_t = 0 \tag{4}$$

where $V_x$, $V_y$, are the x and y components of the optical flow of $I(x,y,t)$ and $$\frac{\partial I}{\partial x}, \frac{\partial I}{\partial y}$$

and $$\frac{\partial I}{\partial t}$$

are the derivatives of the image at (x,y,t) in the corresponding directions.

Given the above, the following can be derived:

$$\nabla I^T \cdot \vec{V} = -I_t \tag{5}$$

Eq. (5) has two unknowns. This is known as the aperture problem of optical flow. To find the optical flow, another set of equations is needed, given by some additional constraint. All optical flow methods introduce additional conditions for estimating the actual flow. Methods for optical flow analysis include: the Lucas-Kanade Method as disclosed in: "*An Iterative Image Registration Technique with an Application to Stereo Vision*", Bruce D. Lucas and Takeo Kanade, Proc. of Imaging Understanding Workshop, pp. 121-130, (1981), the Horn-Schunck Method as disclosed in: "*Determining Optical Flow*", Berthold K. P. Horn and Brian G. Schunck, Vol 17, pp 185-203, Artificial Intelligence, (1981), and the Black-Jepson Method as disclosed in: "*Computation of Optical Flow*", S. S. Beauchemin, J. L. Barron, ACM Computing Surveys, Vol. 27, No. 3, (September 1995). It should also be appreciated that discrete optimization methods can also be employed. Other methods are discussed in: "*A Database and Evaluation Methodology for Optical Flow*", Simon Baker, Daniel Scharstein, J. P. Lewis, Stefan Roth, Michael J. Black, Richard Szeliski, International Journal of Computer Vision, Vol. 92, pp. 1-31 (2011). It should be understood that the optical flow methods listed herein are representative and not exhaustive. Therefore the scope of the appended claims should not be limited to only these techniques.

Figure 3:
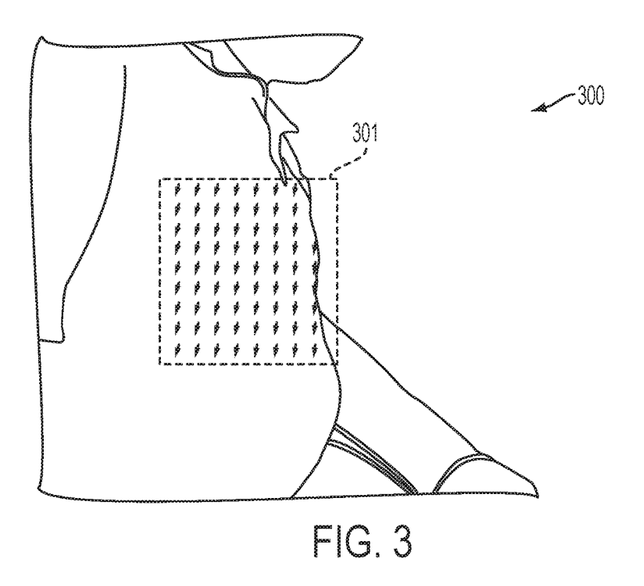
FIG. 3 is an image shown with flow vectors having been computed in a window of pixel locations.

A result of having performed optical flow analysis on an image or a window within an image produces an array of optical flow vectors. FIG. 3 shows an image frame 300 with a plurality of flow vectors generated within window 301. It should be understood that FIG. 3 is for discussion purposes. As such, the scope of the appended claims is not intended to be limited only to flow vectors generated in the windows shown. Moreover, because flow vectors are being generated for each individual pixel location, there would be too many vectors to show on a given image with even a moderate resolution. Thus, it should be appreciated that the flow vectors of FIG. 3 are illustrative for explanatory purposes.

An "optical flow vector", or simply "flow vector", is a vector as is generally understood. A vector has a directional component that corresponds to a temporal variation in intensity, and a magnitude that corresponds to an amount of the variation. A flow vector can be determined as follows.

Calculate, for each image frame $I_t$ of a first portion of the video, where t=1 to N, an image gradient $G_t$ at each (x,y) pixel location as follows:

$$G_t(x, y) = \begin{bmatrix} I_t(x+1, y) - I_t(x, y) \\ I_t(x, y+1) - I_t(x, y) \end{bmatrix} \quad (6)$$

where $I_t(x,y)$ represents values at respective (x,y) pixel locations in the $t^{th}$ image frame Calculate, for each image frame $I_t$ of the first portion of the video, where t=1 to N, a difference $D_t$ at each pixel location (x,y) between image frames $I_t$ and $I_{t-1}$ as follows:

$$D_t(x,y) = I_t(x,y) - I_{t-1}(x,y) \quad (7)$$

where $I_t(x,y)$ represents values at respective (x,y) pixel locations in the $t^{th}$ image frame, and $I_{t-1}(x,y)$ represents values at respective (x,y) pixel locations in the $(t-1)^{th}$ image frame.

Calculate, for each image frame $I_t$ of the first portion of the video, where t=1 to N, a flow vector $F_t$ at each pixel location (x,y) along a direction of the gradient, as follows:

$$F_t(x, y) = \frac{D_t(x, y) G_t(x, y)}{\|G_t(x, y)\|^2}. \quad (8)$$

A "correlated flow field V" captures how the flow vectors at different locations in the image frames are correlated to each other. In accordance herewith, a correlated flow field is determined for the first portion of the video. In one embodiment, the correlated flow field for the first portion of the video is given by:

$$V = \underset{U(x,y) \in W(x,y)}{\operatorname{argmax}} \sum_{t=1}^{N} \left( \sum_{x,y} F_t(x, y) \cdot U(x, y) \right)^2 \quad (9)$$

where W(x,y) is a m×n×2 matrix with unit Frobenius norm, m is a number of rows of $F_t$, and n is a number of columns of $F_t$.

"Velocity $vel_t$" is a projection of $F_t$ in a direction of the correlated flow field V for the $t^{th}$ image frame. The velocity is computed for each image frame in the second portion of the video. In one embodiment, the velocity for the $t^{th}$ image frame is given by:

$$vel_t = \sum_{(x,y)} (F_t(x, y) \cdot V). \quad (10)$$

An "integrated signal" is obtained by integrating the velocities over the image frames of the second portion of the video. The integrated signal corresponds to thoracoabdominal movement.

"Thoracoabdominal movement" of the thoracic cage and abdominal wall due to the expansion and retraction during patient respiration. Although separate systems, movement of the chest cage and abdominal wall during respiration is relatively synchronous in healthy individuals. Asynchrony in thoracoabdominal movement can be a sign of respiratory dysfunction.

"Respiration rate" refers to the number of breaths (inspiration and expiration) that the subject takes over a period of time. A respiration rate is determined for the subject by a number of cycles in the integrated signal that occur over the timeframe of the second portion of the video, typically in number of breaths per minute. The respiration rate can be communicated to a storage device, a display device, and/or a remote device over a network.

It should be appreciated that the steps of "receiving", "determining", "computing", "calculating", "integrating", "performing" and the like, as used herein, include the application of various mathematical operations applied to data according to any specific context or for any specific purpose. It should be appreciated that such steps may be facilitated or otherwise effectuated by a processor executing machine readable program instructions retrieved from a memory or storage device.

Flow Diagram of One Embodiment

Figure 4:
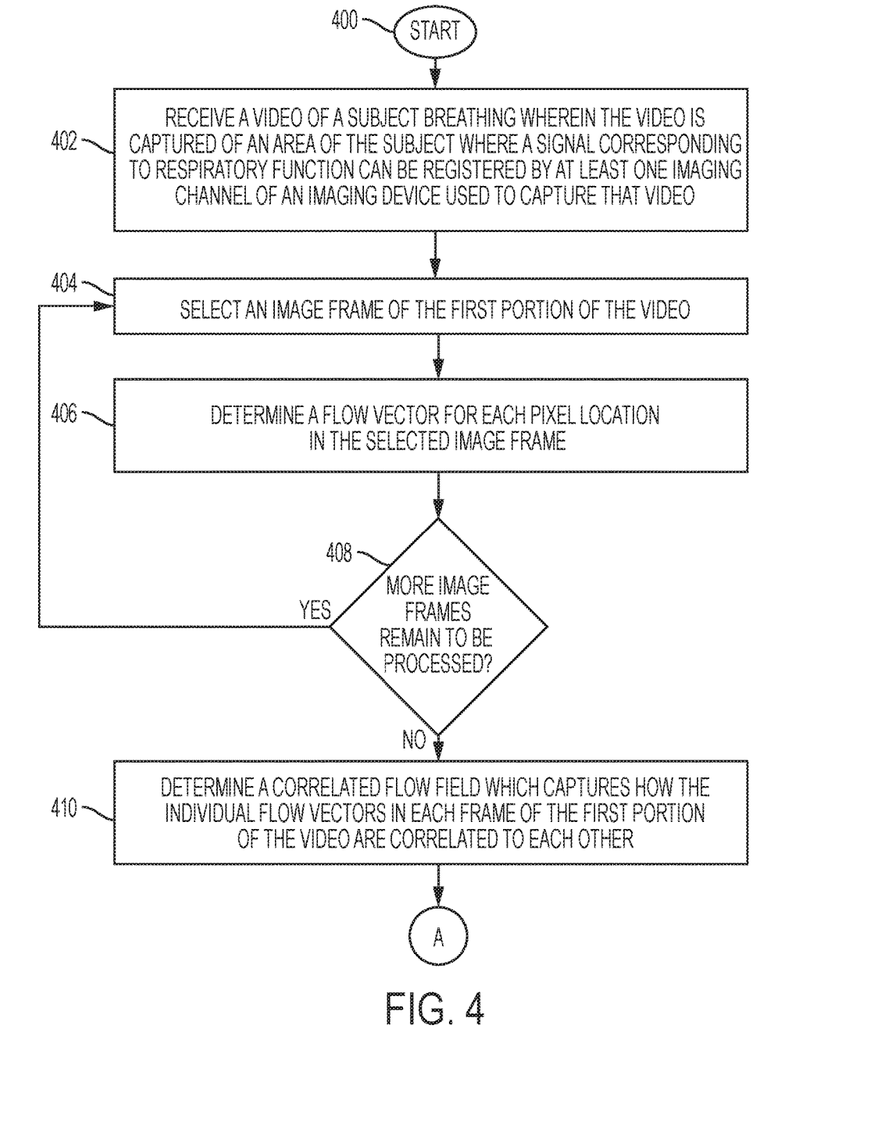
FIG. 4 is a flow diagram which illustrates one example embodiment of the present method for determining a respiration rate from a video of a subject while breathing.

Reference is now being made to the flow diagram of FIG. 4 which illustrates one example embodiment of the present method for determining a respiration rate from a video of a subject while breathing. Flow processing begins at step 400 and immediately proceeds to step 402.

At step 402, receive a video of a subject breathing wherein the video is captured of an area of the subject where a signal corresponding to respiratory function can be registered by at least one imaging channel of an imaging device used to capture that video. The video comprises T time-sequential image frames with a first portion comprising at least 10 seconds of video for a total of N image frames, and a second portion comprising M image frames, where N+M=T.

At step 404, select an image frame of the first portion of the video for processing. The image frames are selected from 1 to N and can be selected manually or automatically.

At step 406, determine a flow vector for each pixel location in the selected image frame.

At step 408, a determination is made whether more image frames remain to be processed. If so, then processing repeats with respect to step 404 wherein a next image frame of the first portion of the video is selected. Processing repeats until flow vectors have been determined for all image frames in the first portion of the video.

At step 410, determine a correlated flow field which captures how the individual flow vectors in each image frame of the first portion of the video are correlated to each other.

Figure 5:
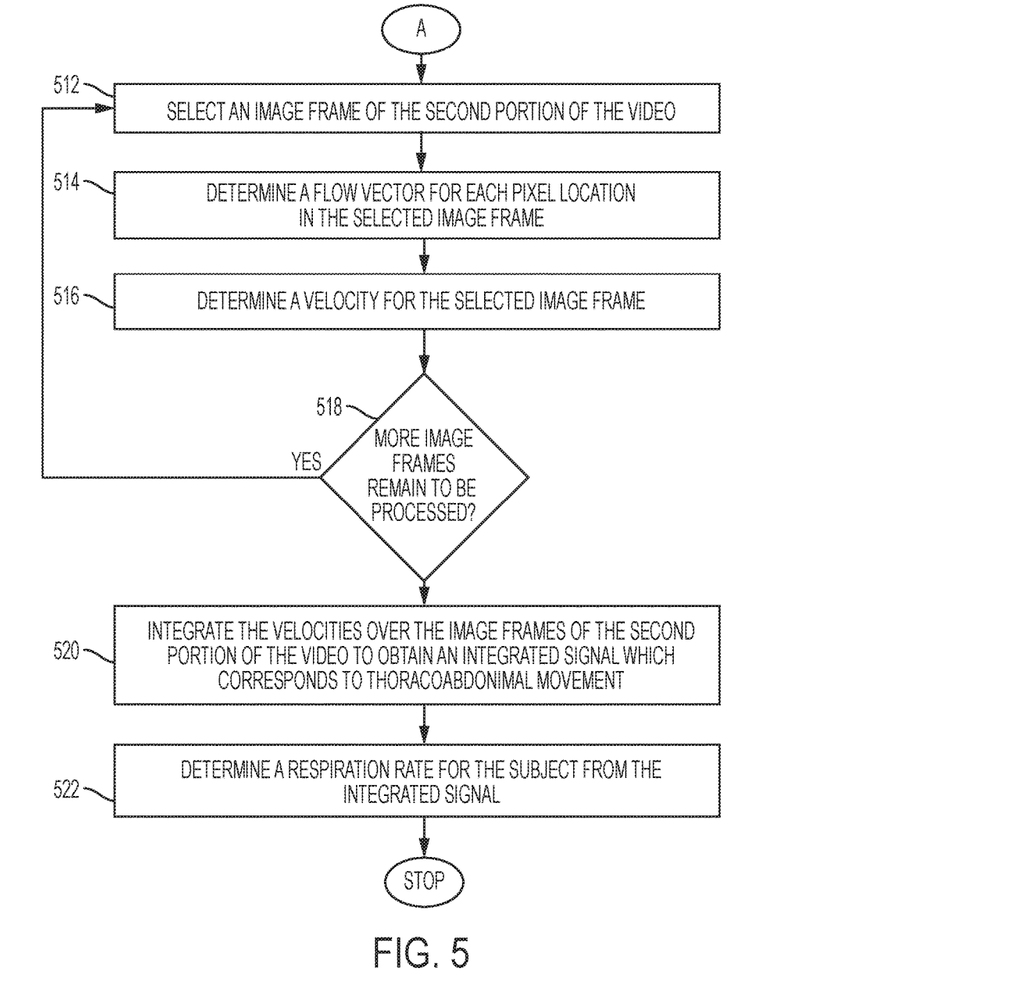
FIG. 5 is a continuation of the flow diagram of FIG. 4 with flow processing continuing with respect to node A.

Reference is now being made to the flow diagram of FIG. 5 which is a continuation of the flow diagram of FIG. 4 with flow processing continuing with respect to node A.

At step 512, select an image frame of the second portion of the video for processing. The image frames are selected from 1 to M and can be selected manually or automatically.

At step 514, determine a flow vector for each pixel location in this image frame.

At step 516, determine a velocity for the selected image frame.

At step 518, a determination is made whether more image frames remain to be processed. If so, then processing repeats with respect to step 512 wherein a next image frame of the second portion of the video is selected. Processing repeats until all image frames in the second portion of the video have been processed accordingly.

At step 520, integrate the velocities over the image frames of the second portion of the video to obtain an integrated signal which corresponds to thoracoabdominal movement.

At step 522, determine a respiration rate for the subject from the integrated signal. In this embodiment further processing stops. In another embodiment, the respiration rate is analyzed to determine whether the patient has a respiratory dysfunction or is in respiratory distress. If so then an alert is generated. The alert may take the form of a message displayed on a display device or a sound activated at, for example, a nurse's station. The alert may take the form of a colored or blinking light which provides a visible indication that an alert condition exists. The alert can be a text, audio, and/or video message. The alert may be communicated to one or more remote devices over a wired or wireless network. The alert may be sent directly to a handheld wireless cellular device of a medical professional.

It should be understood that the flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims. All or portions of the flow diagrams may be implemented partially or fully in hardware in conjunction with machine readable/executable program instructions.

Block Diagram of Image Processing System

Figure 6:
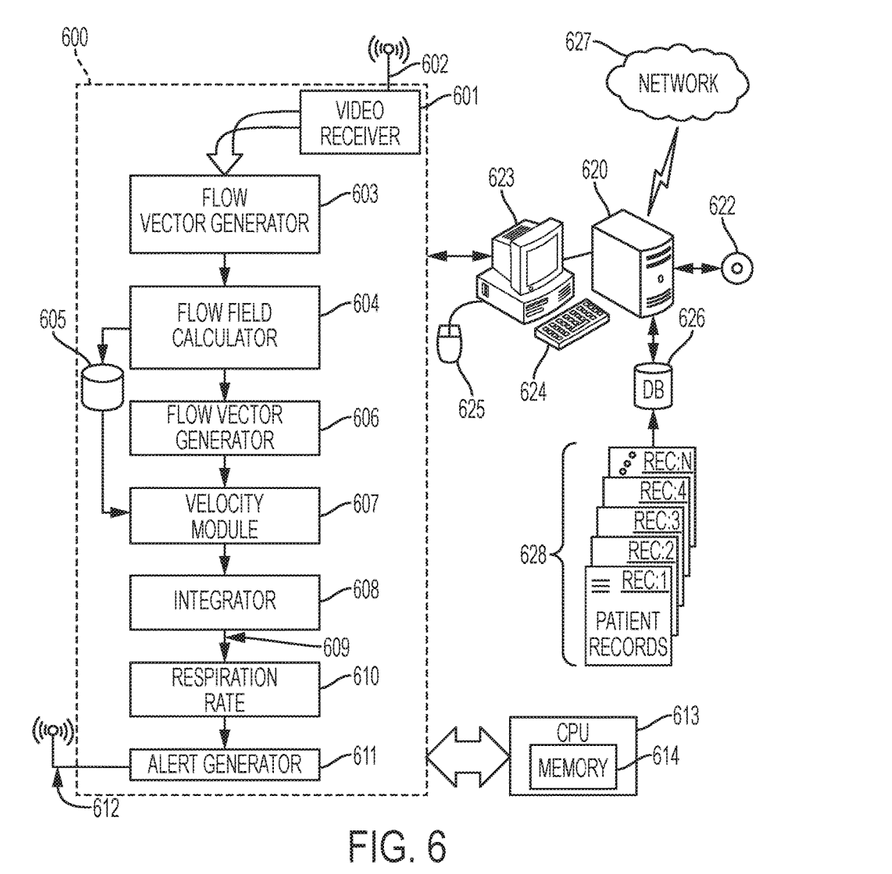
FIG. 6 is a functional block diagram of one example image processing system for processing a video of a subject in accordance with the embodiment described with respect to the flow diagrams of FIGS. 4 and 5.

Reference is now being made to FIG. 6 which shows a block diagram of one example image processing system for processing a video of a subject in accordance with the embodiment described with respect to the flow diagrams of FIGS. 4 and 5.

Video Receiver 601 wirelessly receives the video of the subject via antenna 602 having been transmitted thereto from the imaging device 200 of FIG. 2 using communication element 202. Flow Vector Generator 603 determines a flow vector for each pixel location in each image frame of the first portion of the received video. Flow Field Calculator 604 determines a correlated flow field which captures how the individual flow vectors in each image frame of the first portion of the video are correlated to each other. The correlated flow field is stored to storage device 605. Flow Vector Generator 606 determines a flow vector for each pixel location in each image frame of the second portion of the received video. It should be appreciated that, in other embodiments, Flow Vector Generators 603 and 606 comprise a single unit or processing module. Velocity Module 607 receives the flow vectors on a per-frame basis, retrieves the correlated flow field from storage device 605, and proceeds to determine a velocity for each image frame of the second portion of the video with the velocity being a projection of the flow vectors in a direction of the correlated flow field V for each of the image frames. Integrator Module 608 receives the velocities on a per-frame basis and proceeds to integrate the velocities over the image frames of the second portion of the video to obtain an integrated signal 609 which corresponds to thoracoabdominal movement. Respiration Rate Module 610 receives the integrated signal and proceeds to determine a respiration rate for the subject. Alert Generator 611 initiates an alert signal via antenna 612 in response to the respiration rate not being within acceptable parameters. Central Processing Unit (CPU) 613 retrieves machine readable program instructions from a memory 614 and is provided to facilitate the functionality of any of the modules of the system 600. CPU 613, operating alone or in conjunction with other processors, may be configured to assist or otherwise perform the functionality of any of the modules or processing units of the system 600, as well as facilitating communication between the system 600 and the workstation 620.

Workstation 620 is shown generally comprising a computer case which houses various components such as a motherboard with a microprocessor and memory, a network card, a video card, a hard drive capable of reading/writing to machine readable media 622 such as a floppy disk, optical disk, CD-ROM, DVD, magnetic tape, and the like, and other software and hardware as is needed to perform the functionality of a computer workstation. The workstation includes a display device 623, such as a CRT, LCD, or touchscreen display, for displaying information, image frames, vector magnitudes, vector intensities, optical flow vectors, computed values, patient medical information, and the like, which are produced or are otherwise generated by any of the modules or processing units of the video processing system 600. A user can view any such information and make a selection from various menu options displayed thereon. Keyboard 624 and mouse 625 effectuate a user input or selection. It should be appreciated that the workstation has an operating system and other specialized software configured to display alphanumeric values, menus, scroll bars, dials, slideable bars, pull-down options, selectable buttons, and the like, for entering, selecting, modifying, and accepting information needed for performing various aspects of the methods disclosed herein.

A user may use the workstation to identify a set of image frames of interest, set various parameters, and other facilitate the functionality of any of the modules or processing units of the video processing system 600. A user or technician may utilize the workstation to select image frames for processing, modify, add or delete flow vectors or move a window around an image or re-size a window in an image as is deemed appropriate. The user may adjust various parameters being utilized, group pixels together, or dynamically adjust in real-time, system or settings of any device used to capture the video images.

User inputs and selections may be stored/retrieved to/from any of the storage devices 605, 622 and 626. Default settings and initial parameters can be retrieved from any of the storage devices. The system 600 may communicate to one or more remote devices over network 627, utilizing a wired, wireless, or cellular communication protocol. Although shown as a desktop computer, it should be appreciated that the workstation can be a laptop, mainframe, tablet, notebook, smartphone, or a special purpose computer such as an ASIC, or the like. The embodiment of the workstation is illustrative and may include other functionality known in the arts.

The workstation implements a database in storage device 626 wherein records are stored, manipulated, and retrieved in response to a query. Such records, in various embodiments, take the form of patient medical history stored in association with information identifying the patient (collectively at 628). It should be appreciated that database 626 may be the same as storage device 605 or, if separate devices, may contain some or all of the information contained in either device. Although the database is shown as an external device, the database may be internal to the workstation mounted, for example, on a hard drive.

Any of the components of the workstation may be placed in communication with any of the modules of system 600 or any devices placed in communication therewith. Moreover, any of the modules of system 600 can be placed in communication with storage device 626 and/or computer readable media 622 and may store/retrieve therefrom data, variables, records, parameters, functions, and/or machine readable/executable program instructions, as needed to perform their intended functionality. Further, any of the modules or processing units of the system 600 may be placed in communication with one or more remote devices over network 627. It should be appreciated that some or all of the functionality performed by any of the modules or processing units of system 600 can be performed, in whole or in part, by the workstation. The embodiment shown is illustrative and should not be viewed as limiting the scope of the appended claims strictly to that configuration. Various modules may designate one or more components which may, in turn, comprise software and/or hardware designed to perform the intended function.

The teachings hereof can be implemented in hardware or software using any known or later developed systems, structures, devices, and/or software by those skilled in the applicable arts without undue experimentation from the functional description provided herein with a general knowledge of the relevant arts. One or more aspects of the methods described herein are intended to be incorporated in an article of manufacture. The article of manufacture may be shipped, sold, leased, or otherwise provided separately either alone or as part of a product suite or a service.

The above-disclosed and other features and functions, or alternatives thereof, may be desirably combined into other different systems or applications. Presently unforeseen or unanticipated alternatives, modifications, variations, or improvements may become apparent and/or subsequently made by those skilled in this art which are also intended to be encompassed by the following claims. The teachings of any publications referenced herein are hereby incorporated in their entirety by reference thereto.

What is claimed is:

1. A computer implemented method for determining a respiration rate from a video of a subject while breathing, the method comprising:

receiving T time-sequential image frames of a video of a subject breathing, the video being captured of an area of the subject where a signal corresponding to respiratory function can be registered by at least one imaging channel of an imaging device used to capture that video, the video comprising a first portion of at least 10 seconds of video for a total of N image frames, and a second portion of M image frames, where N+M=T;

for each image frame $I_t$, where t=1 to N, determining a flow vector $F_t(x,y)$ for each (x,y) pixel location;

determining a correlated flow field V which captures how the individual flow vectors in each image frame are correlated to each other;

for each image frame $I_t$, where t=1 to M:
determining a flow vector $F_t(x,y)$ at each (x,y) pixel location; and
determining a velocity $vel_t$ for the $t^{th}$ image frame;

integrating the velocities over the image frames of the second portion of the video to obtain an integrated signal corresponding to thoracoabdominal movement; and determining a respiration rate for the subject from the integrated signal.

2. The computer implemented method of claim 1, wherein determining a flow vector $F_t$ at each (x,y) pixel location in the $t^{th}$ image frame comprises:

$$F_t(x, y) = \frac{D_t(x, y)G_t(x, y)}{\|G_t(x, y)\|^2}$$

where $G_t(x,y)$ is a gradient determined at respective (x,y) pixel locations, and $D_t(x,y)$ is a difference determined at respective (x,y) pixel locations.

3. The computer implemented method of claim 2, wherein determining a gradient $G_t$ at respective (x,y) pixel locations comprises:

$$G_t(x, y) = \begin{bmatrix} I_t(x+1, y) - I_t(x, y) \\ I_t(x, y+1) - I_t(x, y) \end{bmatrix}$$

where $I_t(x,y)$ represents values at respective (x,y) pixel locations in the $t^{th}$ image frame.

4. The computer implemented method of claim 2, wherein determining a difference $D_t$ at respective (x,y) pixel locations comprises:

$$D_t(x,y) = I_t(x,y) - I_{t-1}(x,y)$$

where $I_t(x,y)$ represents values at respective (x,y) pixel locations in the $t^{th}$ image frame, and $I_{t-1}(x,y)$ represents values at respective (x,y) pixel locations in the $(t-1)^{th}$ image frame.

5. The computer implemented method of claim 1, wherein determining a correlated flow field V for the first portion of the video comprises:

$$V = \underset{U(x,y) \in W(x,y)}{\operatorname{argmax}} \sum_{t=1}^{N} \left( \sum_{x,y} F_t(x, y) \cdot U(x, y) \right)^2$$

where W(x,y) is a m×n×2 matrix with unit Frobenius norm, m is a number of rows of $F_t$, and n is a number of columns of $F_t$.

6. The computer implemented method of claim 1, wherein the velocity $vel_t$ is a projection of $F_t$ in a direction of the correlated flow field V for the $t^{th}$ image frame, and comprises:

$$vel_t = \sum_{(x,y)} (F_t(x, y) \cdot V).$$

7. The computer implemented method of claim 1, wherein the respiration rate is determined by a number of cycles in the integrated signal over the timeframe of the second portion of the video.

8. The computer implemented method of claim 1, wherein the video is a streaming video and the respiration rate is determined in real-time.

9. The computer implemented method of claim 1, further comprising communicating the respiration rate to any of: a storage device, a display, and a remote device over a network.

10. A system for determining a respiration rate from a video of a subject while breathing, the system comprising:
   a storage device; and
   a processor executing machine readable instructions for performing:
      receiving T time-sequential image frames of a video of a subject breathing, the video being captured of an area of the subject where a signal corresponding to respiratory function can be registered by at least one imaging channel of an imaging device used to capture that video, the video comprising a first portion of at least 10 seconds of video for a total of N image frames, and a second portion of M image frames, where N+M=T;
      for each image frame $I_t$, where t=1 to N, determining a flow vector $F_t(x,y)$ for each (x,y) pixel location;
      determining a correlated flow field V which captures how the individual flow vectors in each image frame are correlated to each other;
      for each image frame $I_t$, where t=1 to M:
         determining a flow vector $F_t(x,y)$ at each (x,y) pixel location; and
         determining a velocity $vel_t$ for the $t^{th}$ image frame;
      integrating the velocities over the image frames of the second portion of the video to obtain an integrated signal corresponding to thoracoabdominal movement;
      determining a respiration rate for the subject from the integrated signal; and
      communicating the respiration rate to the storage device.

11. The system of claim 10, wherein determining a flow vector $F_t$ at each (x,y) pixel location in the $t^{th}$ image frame comprises:

$$F_t(x, y) = \frac{D_t(x, y) G_t(x, y)}{\|G_t(x, y)\|^2}$$

where $G_t(x,y)$ is a gradient determined at respective (x,y) pixel locations, and $D_t(x,y)$ is a difference determined at respective (x,y) pixel locations.

12. The system of claim 11, wherein determining a gradient $G_t$ at respective (x,y) pixel locations comprises:

$$G_t(x, y) = \begin{bmatrix} I_t(x+1, y) - I_t(x, y) \\ I_t(x, y+1) - I_t(x, y) \end{bmatrix}$$

where $I_t(x,y)$ represents values at respective (x,y) pixel locations in the $t^{th}$ image frame.

13. The system of claim 11, wherein determining a difference $D_t$ at respective (x,y) pixel locations comprises:

$$D_t(x,y) = I_t(x,y) - I_{t-1}(x,y)$$

where $I_t(x,y)$ represents values at respective (x,y) pixel locations in the $t^{th}$ image frame, and $I_{t-1}(x,y)$ represents values at respective (x,y) pixel locations in the $(t-1)^{th}$ image frame.

14. The system of claim 10, wherein determining a correlated flow field V for the first portion of the video comprises:

$$V = \underset{U(x,y) \in W(x,y)}{\operatorname{argmax}} \sum_{t=1}^{N} \left( \sum_{x,y} F_t(x, y) \cdot U(x, y) \right)^2$$

where W(x,y) is a m×n×2 matrix with unit Frobenius norm, m is a number of rows of $F_t$, and n is a number of columns of $F_t$.

15. The system of claim 10, wherein the velocity $vel_t$ is a projection of $F_t$ in a direction of the correlated flow field V for the $t^{th}$ image frame, and comprises:

$$vel_t = \sum_{(x,y)} (F_t(x, y) \cdot V).$$

16. The system of claim 10, wherein the respiration rate is determined by a number of cycles in the integrated signal over the timeframe of the second portion of the video.

17. The system of claim 10, wherein the video is a streaming video and the respiration rate is determined in real-time.

18. The system of claim 10, further comprising communicating the respiration rate to any of: a display device, and a remote device over a network.

* * * * *